United States Patent [19]
Borzatta et al.

[11] Patent Number: 5,514,738
[45] Date of Patent: May 7, 1996

[54] 1-HYDROCARBYLOXY-PIPERIDINE COMPOUNDS CONTAINING SILANE GROUPS FOR USE AS STABILIZERS FOR ORGANIC MATERIALS

[75] Inventors: Valerio Borzatta, Bologna; Primo Carrozza, Verona, both of Italy; Ramanathan Ravichandran, Nanuet, N.Y.

[73] Assignee: Ciba-Geigy Corporation, Tarrytown, N.Y.

[21] Appl. No.: 374,058

[22] Filed: Jan. 19, 1995

[30] Foreign Application Priority Data

Jan. 24, 1994 [IT] Italy .................... MI94A0102

[51] Int. Cl.⁶ .................... C08K 5/3435
[52] U.S. Cl. .................... 524/102; 252/400.3; 546/14; 528/22
[58] Field of Search .................... 252/400.3; 524/102; 546/14; 528/22

[56] References Cited

U.S. PATENT DOCUMENTS

| | | | |
|---|---|---|---|
| 4,177,186 | 12/1979 | Rody et al. | 546/14 |
| 4,778,838 | 10/1988 | Greco et al. | 524/99 |
| 4,859,759 | 8/1989 | Maycock et al. | 528/27 |
| 4,895,885 | 1/1990 | Foster et al. | 524/99 |
| 4,921,962 | 5/1990 | Galbo et al. | 546/184 |
| 4,927,898 | 5/1990 | King, III et al. | 528/27 |
| 4,946,880 | 8/1990 | Costanzi et al. | 524/96 |
| 4,948,888 | 8/1990 | Greco et al. | 544/69 |
| 4,977,259 | 12/1990 | Greco et al. | 544/69 |
| 5,021,481 | 6/1991 | Galbo et al. | 524/99 |
| 5,051,458 | 9/1991 | Costanzi et al. | 524/99 |
| 5,321,066 | 6/1994 | Carrozza et al. | 546/14 |

FOREIGN PATENT DOCUMENTS

| | | |
|---|---|---|
| 162524 | 11/1985 | European Pat. Off. . |
| 244026 | 11/1987 | European Pat. Off. . |
| 343717 | 11/1989 | European Pat. Off. . |
| 388321 | 9/1990 | European Pat. Off. . |
| 461071 | 12/1991 | European Pat. Off. . |
| 480466 | 4/1992 | European Pat. Off. . |
| 491659 | 6/1992 | European Pat. Off. . |
| 234682 | 4/1986 | German Dem. Rep. . |
| 234683 | 4/1986 | German Dem. Rep. . |

OTHER PUBLICATIONS

Chem. Abst. 106:19478r of DD 234,683.
Chem. Abst. 106: 5979t of DD 234,682.
Derw. abst. 86–205177/32 of DD 234,683.
Derw. Abst. 90–284499/38 of EP 388,321.
Derw. Abst. 86–205176/32 of DD 234–682.

Primary Examiner—Kriellion S. Morgan
Attorney, Agent, or Firm—Luther A. R. Hall

[57] ABSTRACT

New stabilizers of the formula (I)

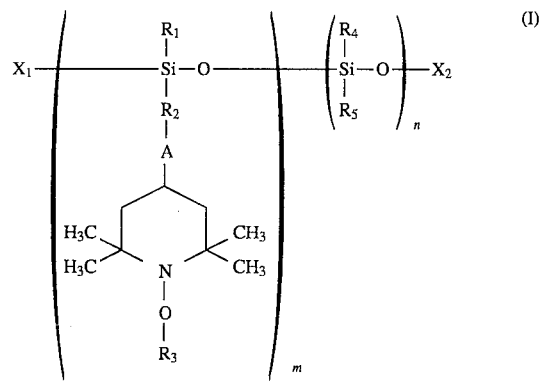

in which
m+n is a number from 1 to 100 and n varies from zero to 90% of the sum of m+n,
A is —O— or

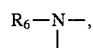

where $R_6$ is e.g. hydrogen or $C_1$–$C_{18}$alkyl, $R_1$ and $R_4$ which can be identical or different are $C_1$–$C_8$alkyl, phenyl, $C_1$–$C_8$alkoxy, OH, ONa or OK, $R_2$ is $C_2$–$C_{12}$alkylene or also a direct bond if A is —O— and $R_1$ and $R_4$ are $C_1$–$C_8$alkyl or phenyl, $R_3$ is $C_1$–$C_{18}$alkyl, $C_5$–$C_{12}$cycloalkyl, $C_2$–$C_{18}$alkenyl, $C_5$–$C_{12}$cycloalkenyl, $C_7$–$C_{12}$aralkyl, a saturated or unsaturated radical of a bicyclic or tricyclic $C_7$–$C_{12}$hydrocarbon or $C_6$–$C_{10}$aryl which is unsubstituted or substituted by $C_1$–$C_8$alkyl, $R_5$ is hydrogen, $C_1$–$C_{18}$alkyl, $C_5$–$C_{12}$cycloalkyl or phenyl, $X_1$ is as defined for $R_1$ or is a group $(R_7)_3$SiO— with $R_7$ being $C_1$–$C_8$alkyl, $X_2$ is e.g. hydrogen, Na, K, $C_1$–$C_8$alkyl or a group $(R_7)_3$Si—, and, if m+n is a number from 3 to 10, $X_1$ and $X_2$ together can also be a direct bond.

12 Claims, No Drawings

1-HYDROCARBYLOXY-PIPERIDINE COMPOUNDS CONTAINING SILANE GROUPS FOR USE AS STABILIZERS FOR ORGANIC MATERIALS

The present invention relates to novel 1-hydrocarbyloxy-2,2,6,6-tetramethylpiperidine compounds containing silane groups, to their use as light stabilizers, heat stabilizers and oxidation stabilizers for organic materials, in particular synthetic polymers, and to organic materials thus stabilized.

The stabilization of synthetic polymers with 2,2,6,6-tetramethylpiperidine derivatives containing silane groups has been described in various patents, in particular in U.S. Pat. Nos. 4,1777,186, 4,859,759, 4,895,885, 4,946,880 and 4,948,888, in EP Patents 162 524, 244 026, 343 717, 388 321, 461 07 1,480 466 and 491 659 and in East German Patents and 234 683.

The present invention relates to novel compounds of the formula (I)

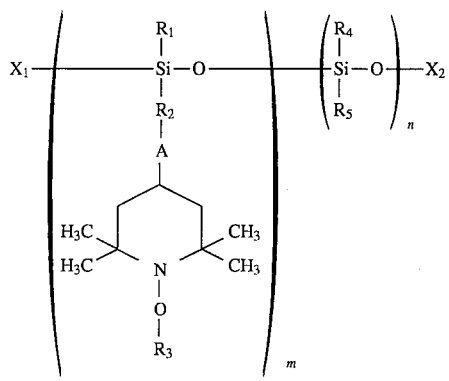

in which m+n is a number from 1 to 100 and n varies from zero to 90% of the sum of m+n, A is —O— or

where $R_6$ is hydrogen, $C_1$–$C_{18}$alkyl or a group of the formula (II)

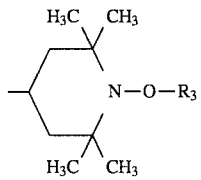

$R_1$ and $R_4$ which can be identical or different are $C_1$–$C_8$alkyl, phenyl, $C_1$–$C_8$alkoxy, OH, ONa or OK, $R_2$ is $C_2$–$C_{12}$alkylene or also a direct bond if A is —O— and $R_1$ and $R_4$ are $C_1$–$C_8$alkyl or phenyl, $R_3$ is $C_1$–$C_{18}$alkyl, $C_5$–$C_{12}$cycloalkyl, $C_2$–$C_{18}$alkenyl, $C_5$–$C_{12}$cycloalkenyl, $C_7$–$C_{12}$aralkyl, a saturated or unsaturated radical of a bicyclic or tricyclic $C_7$–$C_{12}$hydrocarbon or $C_6$–$C_{10}$aryl which is unsubstituted or substituted by $C_1$–$C_8$alkyl, $R_5$ is hydrogen, $C_1$–$C_{18}$alkyl, $C_5$–$C_{12}$cycloalkyl or phenyl, $X_1$ is as defined for $R_1$ or is a group $(R_7)_3$SiO— with $R_7$ being $C_1$–$C_8$alkyl, $X_2$ is hydrogen, Na, K, $C_1$–$C_8$alkyl, a group $(R_7)_3$—Si— or, if n is zero and $R_1$ and $X_1$ are $C_1$–$C_8$alkyl or phenyl, $X_2$ is also a group of the formula (III)

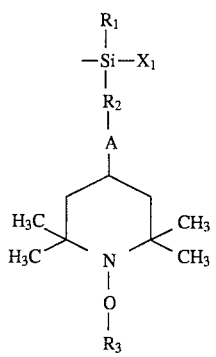

and, if m+n is a number from 3 to 10, $X_1$ and $X_2$ together can also be a direct bond.

Each of the groups A, $R_1$, $R_2$, $R_3$, $R_4$ and $R_5$ can, in the single recurring units of the formula (I), have the same definition or different definitions and, if the compounds of the present invention are copolymeric, they can have a random distribution or a block distribution of the various recurring units.

Examples of alkyl having not more than 18 carbon atoms are methyl, ethyl, propyl, isopropyl, butyl, 2-butyl, isobutyl, t-butyl, pentyl, 2-pentyl, isopentyl, hexyl, heptyl, octyl, 2-ethylhexyl, t-octyl, nonyl, decyl, undecyl, dodecyl, tridecyl, tetradecyl, hexadecyl and octadecyl.

Examples of $C_1$–$C_8$alkoxy are methoxy, ethoxy, propoxy, isopropoxy, butoxy, isobutoxy, t-butoxy, pentoxy, isopentoxy, hexoxy, heptoxy and octoxy.

Examples of $C_5$–$C_{12}$cycloalkyl are cyclopentyl, cyclohexyl, methylcyclohexyl, cycloheptyl, cyclooctyl, cyclodecyl and cyclododecyl. $C_5$–$C_{12}$cycloalkyl also covers a saturated cyclic hydrocarbon radical of 5 to 8 carbon atoms, which is substituted by $C_1$–$C_4$alkyl.

Examples of $C_2$–$C_{18}$alkenyl are vinyl, allyl, 2-methylallyl, butenyl, pentenyl, hexenyl, heptenyl, octenyl, decenyl, dodecenyl, tetradecenyl, hexadecenyl and octadecenyl.

Examples of $C_5$–$C_{12}$cycloalkenyl are cyclopentenyl, cyclohexenyl, methylcyclohexenyl, cycloheptenyl, cyclooctenyl, cyclodecenyl and cyclododecenyl. $C_5$$C_{12}$cycloalkenyl also covers an unsaturated cyclic hydrocarbon radical of 5 to 8 carbon atoms, which is substituted by $C_1$–$C_4$alkyl.

Examples of $C_7$–$C_{12}$aralkyl are benzyl, α-methylbenzyl, α,α-dimethylbenzyl and phenylethyl. $C_7$–$C_9$phenylalkyl is preferred.

Examples of saturated or unsaturated radicals of a bicyclic or tricyclic $C_7$–$C_{12}$ hydrocarbon are bicycloheptyl, bicycloheptenyl, decahydronaphthyl, tetrahydronaphthyl and tricyclodecyl.

Examples of $C_6$–$C_{10}$aryl which is unsubstituted or substituted by alkyl are phenyl, methylphenyl, dimethylphenyl, trimethylphenyl, isopropylphenyl, naphthyl and methylnaphthyl.

Examples of $C_2$–$C_{12}$alkylene are ethylene, propylene, trimethylene, 2-methyltrimethylene, tetramethylene, pentamethylene, hexamethylene, octamethylene, decamethylene, undecamethylene and dodecamethylene. Trimethylene is preferred.

Those compounds of the formula (I) are preferred in which m+n is a number from 1 to 80, n varies from zero to 90% of the sum m+n, A is —O— or

where $R_6$ is hydrogen, $C_1$–$C_{12}$alkyl or a group of the formula (II), $R_1$ and $R_4$ which can be identical or different are $C_1$–$C_6$alkyl, phenyl, $C_1$–$C_6$ alkoxy, OH, ONa or OK, $R_2$ is $C_2$–$C_8$alkylene or also a direct bond if A is —O— and $R_1$ and $R_4$ are $C_1$–$C_6$alkyl or phenyl, $R_3$ is $C_1$–$C_{18}$alkyl, $C_5$–$C_8$cycloalkyl, $C_3$–$C_{12}$alkenyl, $C_5$–$C_8$ cycloalkenyl, $C_7$–$C_9$aralkyl, a saturated or unsaturated radical of a bicyclic or tricyclic $C_7$–$C_{10}$ hydrocarbon or $C_6$–$C_{10}$aryl which is unsubstituted or substituted by $C_1$–$C_4$alkyl, $R_5$ is hydrogen, $C_1$–$C_{18}$alkyl, $C_5$–$C_8$cycloalkyl or phenyl, $X_1$ is as defined for $R_1$ or is a group $(R_7)_3SiO$— with $R_7$ being $C_1$–$C_6$alkyl, $X_2$ is hydrogen, Na, K, $C_1$–$C_6$alkyl, a group $(R_7)_3Si$— or, if n is zero and $R_1$ and $X_1$ are $C_1$–$C_6$alkyl or phenyl, $X_2$ is also a group of the formula (III) and, if m+n is a number from 3 to 10, $X_1$ and $X_2$ together can also be a direct bond.

Those compounds of the formula (I) are particularly preferred in which m+n is a number from 1 to 60, n varies from zero to 90% of the sum of m+n, A is —O— or

where $R_6$ is hydrogen or $C_1$–$C_8$alkyl, $R_1$ and $R_4$ which can be identical or different are $C_1$–$C_4$alkyl, phenyl, $C_1$–$C_4$alkoxy, OH, ONa or OK, $R_2$ is $C_2$–$C_6$alkylene or also a direct bond if A is —O— and $R_1$ and $R_4$ are $C_1$–$C_4$alkyl or phenyl, $R_3$ is $C_1$–$C_{16}$alkyl, $C_5$–$C_7$cycloalkyl, $C_3$–$C_6$alkenyl, $C_5$–$C_7$ cycloalkenyl, benzyl, α-methylbenzyl, α,α-dimethylbenzyl, bicycloheptyl, bicycloheptenyl, decahydronaphthyl or tetrahydronaphthyl, $R_5$ is hydrogen, $C_1$–$C_{16}$alkyl, cyclohexyl or phenyl, $X_1$ is as defined for $R_1$ or a group $(R_7)_3SiO$— with $R_7$ being $C_1$–$C_4$alkyl, $X_2$ is hydrogen, Na, K, $C_1$–$C_4$alkyl, a group $(R_7)_3Si$— or, if n is zero and $R_1$ and $X_1$ are $C_1$–$C_4$alkyl or phenyl, $X_2$ is also a group of the formula (III) and, if m+n is a number from 3 to 10, $X_1$ and $X_2$ together can also be a direct bond.

Those compounds of the formula (I) are of special interest in which m+n is a number from 1 to 50, n varies from zero to 75% of the sum m+n, A is —O— or

where $R_6$ is hydrogen or $C_1$–$C_4$alkyl, $R_1$ and $R_4$ which can be identical or different are $C_1$–$C_3$alkyl, $C_1$–$C_3$alkoxy or OH, $R_2$ is $C_2$–$C_4$alkylene or is also a direct bond if A is —O— and $R_1$ and $R_4$ are $C_1$–$C_3$alkyl, $R_3$ is methyl, $C_6$–$C_{12}$alkyl, cyclopentyl, cyclohexyl, methylcyclohexyl or α-methylbenzyl, $R_5$ is hydrogen, $C_1$–$C_{14}$alkyl or cyclohexyl, $X_1$ is as defined for $R_1$ or is a group $(R_7)_3SiO$— with $R_7$ being $C_1$–$C_3$alkyl, $X_2$ is hydrogen, $C_1$–$C_3$alkyl, a group $(R_7)_3Si$— or, if n is zero and $R_1$ and $X_1$ are $C_1$–$C_3$alkyl, $X_2$ is also a group of the formula (III) and, if m+n is a number from 3 to 10, $X_1$ and $X_2$ together can also be a direct bond.

Those compounds of the formula (I) are of particular interest in which m+n is a number from 1 to 40, n varies from zero to 50% of the sum m+n, A is —O—, $R_1$ and $R_4$ which can be identical or different are methyl, methoxy, ethoxy or OH, $R_2$ is trimethylene or is also a direct bond if A is —O— and $R_1$ and $R_4$ are methyl, $R_3$ is methyl, $C_7$–$C_9$alkyl or cyclohexyl, $R_5$ is $C_1$–$C_{12}$alkyl, $X_1$ is as defined for $R_1$ or is a group $(CH_3)_3SiO$— and $X_2$ is hydrogen, methyl, ethyl, a group $(CH_3)_3Si$— or, if n is zero and $R_1$ and $X_1$ are methyl, $X_2$ is also a group of the formula (III) and, if m+n is a number from 3 to 10, $X_1$ and $X_2$ together can also be a direct bond.

The compounds of the present invention can be prepared by various processes known per se.

If $R_2$ is $C_2$–$C_{12}$alkylene, the compounds of the formula (I) can be prepared, for example, by hydrolytic polycondensation of compounds of the formulae (IVa) and (IVb)

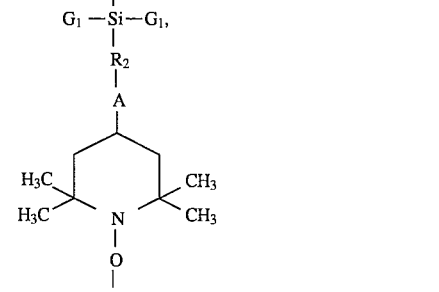

where $G_1$ is Cl or $C_1$–$C_8$alkoxy and $G_2$ is Cl, $C_1$–$C_8$ alkoxy or phenyl, as reported, for example, in U.S. Pat. No. 4,946,880, or, if $R_1$ and $R_4$ are $C_1$–$C_8$alkyl or phenyl, by reaction of a compound of the formula (V)

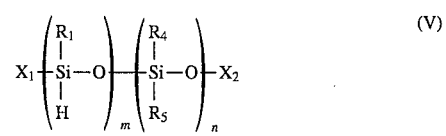

with a compound of the formula (VI)

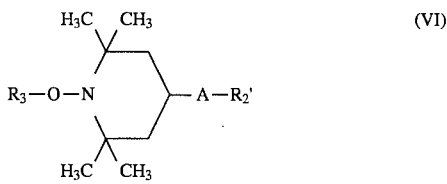

with $R_2'$ being $C_2$–$C_{12}$alkenyl, in the presence of catalytic quantities of the Pt or Rh complex as described, for example, in U.S. Pat. No. 5,051,458 and EP Patent 388 321.

If $R_2$ is a direct bond, the compounds of the formula (I) can be prepared, for example, by reacting a compound of the formula (V) with a piperidinol of the formula (VII)

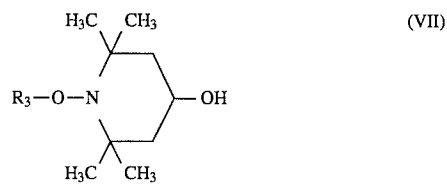

in the presence of catalytic quantifies of a complex of Pt, Rh or Pd, as described, for example, in U.S. Pat. No. 4,895,885.

The compounds of the formula (V) are commercially available or can be prepared by known processes. The compounds of the formula (VI) are prepared, for example, as indicated in U.S. Pat. No. 4,946,880, the group $R_3O$— in the 1-position of the piperidyl group being introduced according to the processes disclosed in U.S. Pat. No. 4,921,962.

The compounds of the formula (VII) are prepared, for example, as reported in U.S. Pat. No. 5,021,481.

The compounds of the present invention are highly effective in improving the light stability, heat stability and oxidation stability of organic materials, in particular synthetic polymers and copolymers, and, owing to their high resistance to volatilization, are particularly suitable for stabilizing polypropylene fibres, especially in the presence of flame retardants, or polyethylene films, particularly in the presence of pesticides.

Examples of such organic materials which can be stabilized are:

1. Polymers of monoolefins and diolefins, for example polypropylene, polyisobutylene, polybut-1-ene, poly-4-methylpent-1-ene, polyisoprene or polybutadiene, as well as polymers of cycloolefins, for instance of cyclopentene or norbornene, polyethylene (which optionally can be crosslinked), for example high density polyethylene (HDPE), low density polyethylene (LDPE), linear low density polyethylene (LLDPE), branched low density polyethylene (BLDPE).

Polyolefins, i.e. the polymers of monoolefins exemplified in the preceding paragraph, preferably polyethylene and polypropylene, can be prepared by different, and especially by the following, methods:

a) radical polymerisation (normally under high pressure and at elevated temperature).

b) catalytic polymerisation using a catalyst that normally contains one or more than one metal of groups IVb, Vb, VIb or VIII of the Periodic Table. These metals usually have one or more than one ligand, typically oxides, halides, alcoholates, esters, ethers, amines, alkyls, alkenyls and/or aryls that may be either π- or σ-coordinated. These metal complexes may be in the free form or fixed on substrates, typically on activated magnesium chloride, titanium(III) chloride, alumina or silicon oxide. These catalysts may be soluble or insoluble in the polymerisation medium. The catalysts can be used by themselves in the polymerisation or further activators may be used, typically metal alkyls, metal hydrides, metal alkyl halides, metal alkyl oxides or metal alkyloxanes, said metals being elements of groups Ia, IIa and/or IIIa of the Periodic Table. The activators may be modified conveniently with further ester, ether, amine or silyl ether groups. These catalyst systems are usually termed Phillips, Standard Oil Indiana, Ziegler (-Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/ propylene copolymers, linear low density polyethylene (LLDPE) and mixtures thereof with low density polyethylene (LDPE), propylene/but-1-ene copolymers, propylene/ isobutylene copolymers, ethylene/but-1-ene copolymers, ethylene/hexene copolymers, ethylene/methylpentene copolymers, ethylene/heptene copolymers, ethylene/octene copolymers, propylene/butadiene copolymers, isobutylene/ isoprene copolymers, ethylene/alkyl acrylate copolymers, ethylene/alkyl methacrylate copolymers, ethylene/vinyl acetate copolymers and theft copolymers with carbon monoxide or ethylene/acrylic acid copolymers and theft salts (ionomers) as well as terpolymers of ethylene with propylene and a diene such as hexadiene, dicyclopentadiene or ethylidene-norbornene; and mixtures of such copolymers with one another and with polymers mentioned in 1) above, for example polypropylene/ethylene-propylene copolymers, LDPE/ethylene-vinyl acetate copolymers (EVA), LDPE/ ethylene-acrylic acid copolymers (EAA), LLDPE/EVA, LLDPE/EAA and alternating or random polyalkylene/carbon monoxide copolymers and mixtures thereof with other polymers, for example polyamides.

4. Hydrocarbon resins (for example $C_5$–$C_9$) including hydrogenated modifications thereof (e.g. tackifiers) and mixtures of polyalkylenes and starch.

5. Polystyrene, poly(p-methylstyrene), poly(α-methylstyrene).

6. Copolymers of styrene or α-methylstyrene with dienes or acrylic derivatives, for example styrene/butadiene, styrene/acrylonitrile, styrene/alkyl methacrylate, styrene/butadiene/alkyl acrylate, styrene/butadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer; and block copolymers of styrene such as styrene/butadiene/ styrene, styrene/isoprene/styrene, styrene/ethylene/butylene/styrene or styrene/ethylene/propylene/styrene.

7. Graft copolymers of styrene or α-methylstyrene, for example styrene on polybutadiene, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or AES polymers.

8. Halogen-containing polymers such as polychloroprene, chlorinated rubbers, chlorinated or sulfochlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloride/vinylidene chloride, vinyl chloride/vinyl acetate or vinylidene chloride/vinyl acetate copolymers.

9. Polymers derived from $\alpha,\beta$-unsaturated acids and derivatives thereof such as polyacrylates and polymethacrylates; polymethyl methacrylates, polyacrylamides and polyacrylonitriles, impact-modified with butyl acrylate.

10. Copolymers of the monomers mentioned under 9) with each other or with other unsaturated monomers, for example acrylonitrile/butadiene copolymers, acrylonitrile/alkyl acrylate copolymers, acrylonitrile/alkoxyalkyl acrylate or acrylonitrile/vinyl halide copolymers or acrylonitrile/alkyl methacrylate/butadiene terpolymers.

11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in 1) above.

12. Homopolymers and copolymers of cyclic ethers such as polyalkylene glycols, polyethylene oxide, polypropylene oxide or copolymers thereof with bisglycidyl ethers.

13. Polyacetals such as polyoxymethylene and those polyoxymethylenes which contain ethylene oxide as a comonomer; polyacetals modified with thermoplastic polyurethanes, acrylates or MBS.

14. Polyphenylene oxides and sulfides, and mixtures of polyphenylene oxides with styrene polymers or polyamides.

15. Polyurethanes derived from hydroxyl-terminated polyethers, polyesters or polybutadienes on the one hand and aliphatic or aromatic polyisocyanates on the other, as well as precursors thereof.

16. Polyamides and copolyamides derived from diamines and dicarboxylic acids and/or from aminocarboxylic acids or the corresponding lactams, for example polyamide 4, polyamide 6, polyamide 6/6, 6/10, 6/9, 6/12, 4/6, 12/12, polyamide 11, polyamide 12, aromatic polyamides starting from m-xylene diamine and adipic acid; polyamides prepared from hexamethylenediamine and isophthalic or/and terephthalic acid and with or without an elastomer as modifier, for example poly-2,4,4,-trimethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).

17. Polyureas, polyimides, polyamide-imides and polybenzimidazoles.

18. Polyesters derived from dicarboxylic acids and diols and/or from hydroxycarboxylic acids or the corresponding lactones, for example polyethylene terephthalate, polybutylene terephthalate, poly-1,4-dimethylolcyclohexane terephthalate and polyhydroxybenzoates, as well as block copolyether esters derived from hydroxyl-terminated polyethers; and also polyesters modified with polycarbonates or MBS.

19. Polycarbonates and polyester carbonates.

20. Polysulfones, polyether sulfones and polyether ketones.

21. Crosslinked polymers derived from aldehydes on the one hand and phenols, ureas and melamines on the other hand, such as phenol/formaldehyde resins, urea/formaldehyde resins and melamine/formaldehyde resins.

22. Drying and non-drying alkyd resins.

23. Unsaturated polyester resins derived from copolyesters of saturated and unsaturated dicarboxylic acids with polyhydric alcohols and vinyl compounds as crosslinking agents, and also halogen-containing modifications thereof of low flammability.

24. Crosslinkable acrylic resins derived from substituted acrylates, for example epoxy acrylates, urethane acrylates or polyester acrylates.

25. Alkyd resins, polyester resins and acrylate resins crosslinked with melamine resins, urea resins, polyisocyanates or epoxy resins.

26. Crosslinked epoxy resins derived from polyepoxides, for example from bisglycidyl ethers or from cycloaliphatic diepoxides.

27. Natural polymers such as cellulose, rubber, gelatin and chemically modified homologous derivatives thereof, for example cellulose acetates, cellulose propionates and cellulose butyrates, or the cellulose ethers such as methyl cellulose; as well as rosins and their derivatives.

28. Blends of the aforementioned polymers (polyblends), for example PP/EPDM, Polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO.

29. Naturally occurring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, typically those used as spinning compositions, as well as aqueous emulsions of such materials.

30. Aqueous emulsions of natural or synthetic rubber, e.g. natural latex or latices of carboxylated styrene/butadiene copolymers.

The compounds of the formula (I) are particularly suitable for improving the light stability, heat stability and oxidation stability of polyolefins, especially polyethylene and polypropylene.

The compounds of the formula (I) can be used in mixtures with organic materials in various proportions depending on the nature of the material to be stabilized, on the end use and on the presence of other additives.

In general, it is appropriate to use, for example, 0.01 to 5% by weight of the compounds of the formula (I), relative to the weight of the material to be stabilized, preferably between 0.05 and 1%.

In general, the compounds of the formula (I) can be added to the polymeric materials before, during or after the polymerization or crosslinking of the said materials.

The compounds of the formula (I) can be incorporated in the polymeric materials in the pure form or encapsulated in waxes, oils or polymers.

The compounds of the formula (I) can be incorporated in the polymeric materials by various processes, such as dry mixing in the form of powder, or wet mixing in the form of solutions or suspensions or also in the form of a masterbatch; in such operations, the polymer can be used in the form of powder, granules, solutions, suspensions or in the form of latices.

The materials stabilized with the products of the formula (I) can be used for the production of mouldings, films, tapes, monofilaments, fibres, surface coatings and the like.

If desired, other conventional additives for synthetic polymers, such as antioxidants, UV absorbers, nickel stabilizers, pigments, fillers, plasticizers, antistatic agents, flameproofing agents, lubricants, corrosion inhibitors and metal deactivators, can be added to the mixtures of the compounds of the formula (I) with the organic materials.

Particular examples of additives which can be used in admixture with the compounds of the formula (I) are:

1. Antioxidants 1.1. Alkylated monophenols, for example 2,6-di-tert-butyl-4-methylphenol, 2-tert-butyl- 4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, 2,6-di-nonyl-4-methylphenol, 2,4-dimethyl-6-(1'-methylundec-1'-yl)phenol, 2,4-dimethyl-6-(1'-methylheptadec-1'-yl)phenol, 2,4-dimethyl- 6-(1'-methyltridec-1'-yl)phenol and mixtures thereof.

1.2. Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6-didodecylthiomethyl- 4-nonylphenol.

1.3. Hydroquinones and alkylated hydroquinones, for example 2,6-di-tert-butyl-4-methoxyphenol, 2,5-di-tert-butylhydroquinone, 2,5-di-tert-amylhydroquinone, 2,6-diphenyl- 4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis-(3,5-di-tert-butyl-4-hydroxyphenyl) adipate.

1.4. Tocopherols, for example α-tocopherol, β-tocopherol, δ-tocopherol, δ-tocopherol and mixtures thereof (Vitamin E).

1.5. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis( 6-tert-butyl-2-methylphenol), 4,4'-thiobis-(3, 6-di-sec-amylphenol), 4,4'-bis-(2,6-dimethyl- 4-hydroxyphenyl) disulfide.

1.6. Alkylidenebisphenols, for example 2,2'-methylenebis(6-tert-butyl-4-methylphenol), 2,2'-methylenebis(6-tert-butyl-4-ethylphenol), 2,2'-methylenebis[4-methyl- 6-(α-methylcyclohexyl)phenol], 2,2'-methylenebis(4-methyl-6-cyclohexylphenol), 2,2'-methylenebis( 6-nonyl-4-methylphenol), 2,2'-methylenebis(4,6-di-tert-butylphenol), 2,2'-ethylidenebis( 4,6-di-tert-butylphenol), 2,2'-ethylidenebis(6-ten-butyl-4-isobutylphenol), 2,2'-methylenebis[ 6-(α-methylbenzyl)-4-nonylphenol], 2,2'-methylenebis[6-(α,α-dimethylbenzyl)- 4-nonylphenol], 4,4'-methylenebis(2,6-di-tert-butylphenol), 4,4'-methylenebis(6-tert-butyl- 2-methylphenol), 1,1-bis(5-tert-butyl-4-hydroxy-2-methylphenyl)butane, 2,6-bis(3-tert-butyl- 5-methyl-2-hydroxybenzyl)-4-methylphenol, 1,1,3-tris(5-tert-butyl-4-hydroxy- 2-methylphenyl)butane, 1,1-bis(5-tert-butyl-4-hydroxy-2-methyl-phenyl)-3-n-dodecylmercaptobutane, ethylene glycol bis[3,3-bis(3'-tert-butyl-4'-hydroxyphenyl)butyrate], bis(3-tert-butyl-4-hydroxy-5-methyl-phenyl)dicyclopentadiene, bis[2-(3'-tert-butyl-2'-hydroxy- 5'-methylbenzyl)-6-tert-butyl-4-methylphenyl]terephthalate, 1,1-bis-(3,5-dimethyl- 2-hydroxyphenyl)butane, 2,2-bis-(3,5-di-tert-butyl-4-hydroxyphenyl)propane, 2,2-bis-(5-tert-butyl-4-hydroxy2-methylphenyl)-4-n-dodecylmercaptobutane, 1,1,5,5-tetra-(5-tert-butyl- 4-hydroxy2-methylphenyl)pentane.

1.7. O-, N- and S-benzyl compounds, for example 3,5,3',5'-tetra-tert-butyl-4,4'-dihydroxydibenzyl ether, octadecyl-4-hydroxy-3,5-dimethylbenzylmercaptoacetate, tris-(3,5-di-tert-butyl- 4-hydroxybenzyl)amine, bis(4-tert-butyl-3-hydroxy-2,6-dimethylbenzyl)dithioterephthalate, bis(3,5-di-tert-butyl-4-hydroxybenzyl)sulfide, isooctyl-3,5di-tert-butyl- 4-hydroxybenzylmercaptoacetate.

1.8. Hydroxybenzylated malonates, for example dioctadecyl-2,2-bis-(3,5-di-tert-butyl- 2-hydroxybenzyl)-malonate, di-octadecyl-2-(3-tert-butyl-4-hydroxy-5-methylbenzyl)-malonate, di-dodecylmercaptoethyl-2,2-bis-(3,5-di-tert-butyl-4-hydroxybenzyl)malonate, bis[ 4-(1,1,3,3-tetramethylbutyl)phenyl]-2,2-bis(3,5-di-tert-butyl-4-hydroxybenzyl)malonate.

1.9. Aromatic hydroxybenzyl compounds, for example 1,3, 5-tris-(3,5-di-tert-butyl- 4-hydroxybenzyl)- 2,4,6-trimethylbenzene, 1,4-bis(3,5-di-tert-butyl-4-hydroxybenzyl)-2, 3,5,6-tetramethylbenzene, 2,4,6-tris(3,5-di-tert-butyl-4-hydroxybenzyl)phenol.

1.10. Triazine Compounds, for example 2,4-bis(octylmercapto)-6-(3,5-di-tert-butyl- 4-hydroxyanilino)- 1,3,5-triazine, 2-octylmercapto-4,6-bis(3,5-di-tert-butyl-4-hydroxyanilino)- 1,3,5-triazine, 2-octylmercapto-4,6-bis(3, 5-di-tert-butyl-4-hydroxyphenoxy)- 1,3,5-triazine, 2,4,6-tris(3,5-di-tert-butyl-4-hydroxyphenoxy)-1,2,3-triazine, 1,3,5-tris( 3,5-di-tert-butyl-4-hydroxybenzyl)isocyanurate, 1,3,5-tris(4-tert-butyl-3-hydroxy-2,6-dimethylbenzyl)isocyanurate, 2,4,6-tris(3,5-di-tert-butyl-4-hydroxyphenylethyl)-1,3,5-triazine, 1,3,5-tris(3,5-di-tert-butyl-4-hydroxyphenylpropionyl)-hexahydro-1,3,5-triazine, 1,3,5-tris(3,5-dicyclohexyl-4-hydroxybenzyl)isocyanurate.

1.11. Benzylphosphonates, for example dimethyl-2,5-di-tert-butyl-4-hydroxybenzylphosphonate, diethyl-3,5-di-tert-butyl-4-hydroxybenzylphosphonate, dioctadecyl3,5-di-tert-butyl- 4-hydroxybenzylphosphonate, dioctadecyl-5-tert-butyl-4-hydroxy3-methylbenzylphosphonate, the calcium salt of the monoethyl ester of 3,5-di-tert-butyl-4-hydroxybenzylphosphonic acid.

1.12. Acylaminophenols, for example 4-hydroxylauranilide, 4-hydroxystearanilide, octyl N-(3,5-di-tert-butyl-4-hydroxyphenyl)carbamate.

1.13. Esters of β-(3,5-di-tert-butyl-4-hydroxyphenyl)propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.14. Esters of β-(5-tert-butyl-4-hydroxy-3-methylphenyl)propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.15. Esters of β-(3,5-dicyclohexyl-4-hydroxyphenyl)propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.16. Esters of 3,5-di-tert-butyl-4-hydroxyphenyl acetic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo [2.2.2]octane.

1.17. Amides of β-(3,5-di-tert-butyl-4-hydroxyphenyl)propionic acid e.g. N,N'-bis(3,5-di-tert-butyl- 4-hydroxyphenylpropionyl)hexamethylenediamine, N,N'-bis(3,5-di-tert-butyl-4-hydroxyphenylpropionyl)trimethylenediamine, N,N'-bis(3,5-di-tert-butyl-4-hydroxyphenylpropionyl) hydrazine.

2. UV absorbers and light stabilisers 2.1. 2-(2'-Hydroxyphenyl)benzotriazoles, for example 2-(2'-hydroxy-5'-methylphenyl)benzotriazole, 2-(3',5'-di-tert-butyl-2'-hydroxyphenyl)benzotriazole, 2-(5'-tert-butyl-2'-hydroxyphenyl)benzotriazole, 2-(2'-hydroxy-5'-(1,1,3,3-tetramethylbutyl)phenyl)benzotriazole, 2-(3',5'-di-tert-butyl-2'-hydroxyphenyl)-5-chloro-benzotriazole, 2-(3'-tert-butyl- 2'-hydroxy-5'-methylphenyl)-5-chloro-benzotriazole, 2-(3'-sec-butyl-5'-tert-butyl-2'-hydroxyphenyl)benzotriazole, 2-(2'-hydroxy-4'-octyloxyphenyl)benzotriazole, 2-(3',5'-di-tert-amyl- 2'-hydroxyphenyl)benzotriazole, 2-(3',5'-bis-(α,α-dimethylbenzyl)-2'-hydroxyphenyl)benzotriazole, mixture of 2-(3'-tert-butyl-2'-hydroxy-5'-(2-octyloxycarbonylethyl)phenyl)- 5-chloro-benzotriazole, 2-(3'-tert-butyl-5'-[2-(2-ethylhexyloxy)-carbonylethyl] -2'-hydroxyphenyl)-5-chloro-benzotriazole, 2-(3'-tert-butyl-2'-hydroxy-5'-(2-methoxycarbonylethyl)phenyl)- 5-chloro-benzotriazole, 2-(3'-tert-butyl-2'-hydroxy-5'-(2-methoxycarbonylethyl)phenyl)benzotriazole, 2-(3'-tert-butyl-2'-hydroxy-5'-(2-octyloxycarbonylethyl)phenyl)benzotriazole, 2-(3'-tert-butyl-5'-[2-(2-ethylhexyloxy)carbonylethyl] -2'-hydroxyphenyl)benzotriazole, 2-(3'-dodecyl-2'-hydroxy-5'-methylphenyl)benzotriazole, and 2-(3'-tert-butyl-2'-hydroxy-5'-(2-isooctyloxycarbonylethyl)phenylbenzotriazole, 2,2'-methylene-bis[4-(1,1,3,3-tetramethylbutyl)-6-benzotriazole-2-ylphenol]; the transesterification product of 2-[3'-tert-butyl-5'-(2-methoxycarbonylethyl)-2'-hydroxyphenyl] -2H-benzotriazole with polyethylene glycol 300; [R—CH$_2$CH$_2$—COO(CH$_2$)$_3$ ]$_2$, where R=3'-tert-butyl-4'-hydroxy-5'-2H-benzotriazol-2-ylphenyl.

2.2. 2-Hydroxybenzophenones, for example the 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy derivatives.

2.3. Esters of substituted and unsubstituted benzoic acids, as for example 4-tertbutylphenyl salicylate, phenyl salicylate, octylphenyl salicylate, dibenzoyl resorcinol, bis(4-tert-butylbenzoyl) resorcinol, benzoyl resorcinol, 2,4-di-tertbutylphenyl 3,5-di-tert-butyl- 4-hydroxybenzoate, hexadecyl 3,5-di-tert-butyl-4-hydroxybenzoate, octadecyl 3,5-di-tert-butyl- 4-hydroxybenzoate, 2-methyl-4,6-di-tert-butylphenyl 3,5-di-tert-butyl-4-hydroxybenzoate.

2.4. Acrylates, for example ethyl α-cyano-β,β-diphenylacrylate, isooctyl α-cyano-β,β-diphenylacrylate, methyl α-carbomethoxycinnamate, methyl α-cyano-β-methyl-p-methoxycinnamate, butyl α-cyano-β-methyl-p-methoxycinnamate, methyl α-carbomethoxy-p-methoxycinnamate and N-(β-carbomethoxy-β-cyanovinyl)-2-methylindoline.

2.5. Nickel compounds, for example nickel complexes of 2,2'-thio-bis-[4-(1,1,3,3-tetramethylbutyl)phenol] , such as the 1:1 or 1:2 complex, with or without additional ligands such as n-butylamine, triethanolamine or N-cyclohexyldiethanolamine, nickel dibutyldithiocarbamate, nickel salts of the monoalkyl esters, e.g. the methyl or ethyl ester, of 4-hydroxy- 3,5-di-tert-butylbenzylphosphonic acid, nickel complexes of ketoximes, e.g. of 2-hydroxy-4-methylphenyl undecylketoxime, nickel complexes of 1-phenyl-4-lauroyl-5-hydroxypyrazole, with or without additional ligands.

2.6. Sterically hindered amines, for example bis(2,2,6,6-tetramethyl-piperidyl)sebacate, bis(2,2,6,6-tetramethylpiperidyl)succinate, bis(1,2,2,6,6-pentamethylpiperidyl)sebacate, bis(1,2,2,6,6-pentamethylpiperidyl) n-butyl-3,5-di-tert-butyl-4-hydroxybenzylmalonate, the condensate of 1-(2-hydroxyethyl)-2,2,6,6-tetramethyl-4-hydroxypiperidine and succinic acid, the condensate of N,N'-bis(2,2,6,6-tetramethyl-4-piperidyl)hexamethylenediamine and 4-tert-octylamino-2,6-dichloro-1,3,5-triazine, tris(2,2,6,6-tetramethyl-4-piperidyl) nitrilotriacetate, tetrakis(2,2,6,6-tetramethyl-4- piperidyl)-1,2,3,4-butanetetracarboxylate, 1,1'-(1,2-ethanediyl)bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)- 2-n-butyl-2-(2-hydroxy-3, 5-di-tert-butylbenzyl)malonate, 3-n-octyl- 7,7,9,9-tetramethyl-1,3,8-triazasprio[4.5]decan-2,4-dion, bis(1-octyloxy-2,2,6,6-tetramethylpiperidyl)se bis(1-octyloxy-2,2,6,6-tetramethylpiperidyl)succinate, the condensate of N,N'-bis-(2,2,6,6-tetramethyl-4-piperidyl)hexamethylenediamine and 4-morpholino-2,6-dichloro-1,3,5-triazine, the condensate of 2-chloro-4,6-bis(4-n-butylamino-2,2,6,6-tetramethylpiperidyl)-1,3,5-triazine and 1,2-bis(3-aminopropylamino)ethane, the condensate of 2-chloro-4, 6-di-(4-n-butylamino-1,2,2,6,6-pentamethylpiperidyl)-1,3,5-triazine and 1,2-bis-(3-aminopropylamino)ethane, 8-acetyl-3-dodecyl-7,7,9,9-tetramethyl- 1,3,8-triazaspiro [4.5]decane-2,4-dione, 3-dodecyl-1-(2,2,6,6-tetramethyl-4-piperidyl)pyrrolidin- 2,5-dione, 3-dodecyl-1-(1,2,2,6,6-pentamethyl-4-piperidyl)pyrrolidine- 2,5-dione.

2.7. Oxamides, for example 4,4'-dioctyloxyoxanilide, 2,2'-diethoxyoxanilide, 2,2'-dioctyloxy- 5,5'-di-tert-butoxanilide, 2,2'-didodecyloxy-5,5'-di-tert-butoxanilide, 2-ethoxy-2'-ethyloxanilide, N,N'-bis(3-dimethylaminopropyl)oxamide, 2-ethoxy-5-tert-butyl-2'-ethoxanilide and its mixture with 2-ethoxy-2'-ethyl-5,4'-di-tert-butoxanilide and mixtures of ortho- and para-methoxy-disubstituted oxanilides and mixtures of o- and p-ethoxy-disubstituted oxanilides.

2.8. 2-(2-Hydroxyphenyl)-1,3,5-triazines, for example 2,4, 6-tris(2-hydroxy-4-octyloxyphenyl)- 1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy- 4-octyloxyphenyl)-4,6-bis(4-methylphenyl)-1, 3,5-triazine, 2-(2-hydroxy-4-dodecyloxyphenyl)- 4,6-bis(2,4-dimethylphenyl)-1,3,5-triazine, 2-[2-hydroxy-4-(2hydroxy- 3-butyloxy-propoxy)phenyl]-4,6-bis(2,4-dimethyl)-1,3,5-triazine, 2-[2-hydroxy-4-( 2-hydroxy-3-octyloxy-propyloxy)phenyl]-4,6-bis(2,4-dimethyl)-1,3, 5-triazine.

3. Metal deactivators, for example N,N'-diphenyloxamide, N-salicylal-N'-salicyloyl hydrazine, N,N'-bis(salicyloyl) hydrazine, N,N'-bis(3,5-di-tert-butyl-4-hydroxyphenyl-propionyl) hydrazine, 3-salicyloylamino-1,2,4-triazole, bis(benzylidene)oxalyl dihydrazide, oxanilide, isophthaloyl dihydrazide, sebacoyl bisphenylhydrazide, N,N'-diacetyladipoyl dihydrazide, N,N'-bis(salicyloyl)oxalyl dihydrazide, N,N'-bis(salicyloyl)thiopropionyl dihydrazide.

4. Phosphites and phosphonites, for example triphenyl phosphite, diphenyl alkyl phosphites, phenyl dialkyl phosphites, tris(nonylphenyl) phosphite, trilauryl phosphite, trioctadecyl phosphite, distearyl pentaerythritol diphosphite, tris(2,4-di-tert-butylphenyl) phosphite, diisodecyl pentaerythritol diphosphite, bis(2,4-di-tert-butylphenyl) pentaerythritol diphosphite, bis(2,6-di-tert-butyl-4-methylphenyl)-pentaerythritol diphosphite, diisodecyloxypentaerythritol diphosphite, bis(2,4-di-tert-butyl-6-methylphenyl)pentaerythritol diphosphite, bis(2,4,6-tris(tert-butylphenyl)pentaerythritol diphsophite, tristearyl sorbitol triphosphite, tetrakis(2,4-di-tert-butylphenyl) 4,4'-biphenylene diphosphonite, 6-isooctyloxy- 2,4,8,10-tetra-tert-butyl-12H-dibenz[d,g]-1,3,2-dioxaphosphocin, 6-fluoro-2,4,8,10-tetra-tert-butyl-12-methyl-dibenz[d,g ]-1,3,2-dioxaphosphocin, bis(2,4-di-tert-butyl-6-methylphenyl)methylphosphite bis(2,4-di-tert-butyl-6-methylphenyl)ethylphosphite.

5. Peroxide scavengers, for example esters of β-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(β-dodecylmercapto)propionate.

6. Polyamide stabilisers, for example, copper salts in combination with iodides and/or phosphorus compounds and salts of divalent manganese.

7. Basic co-stabilisers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example calcium stearate, zinc stearate, magnesium behenate, magnesium stearate, sodium ricinoleate and potassium palmitate, antimony pyrocatecholate or tin pyrocatecholate.

8. Nucleating agents, for example, 4-tert-butylbenzoic acid, adipic acid, diphenylacetic acid.

9. Fillers and reinforcing agents, for example, calcium carbonate, silicates, glass fibres, asbestos, talc, kaolin, mica, barium sulfate, metal oxides and hydroxides, carbon black, graphite.

10. Other additives, for example, plasticisers, lubricants, emulsifiers, pigments, optical brighteners, flameproofing agents, antistatic agents and blowing agents.

11. Benzofuranones and indolinones, for example those disclosed in U.S. Pat. No. 4,325,863, U.S. Pat. No. 4,338,244, U.S. Pat. No. 5,175,312, U.S. Pat. No. 5,216,052, U.S. Pat. No. 5,252,643, DE-A-4 316 611, DE-A-4 316 622, DE-A-4 316 876, EP-A-0 589 839 or EP-A-0 591 102 or 3-[4-(2-acetoxyethoxy)phenyl] -5,7-di-tert-butyl-benzofuran-2-one, 5,7-di-tert-butyl-3-[4-(2-stearoyloxyethoxy)phenyl] benzofuran-2-one, 3,3'-bis[5,7-di-tert-butyl-3-(4-[2-hydroxyethoxy]-phenyl)benzofuran- 2-one], 5,7-di-tert-butyl-3-(4-ethoxyphenyl)benzofuran-2-one, 3-(4-acetoxy- 3,5-dimethylphenyl)-5,7-di-tert-butyl-benzofuran-2-one, 3-(3,5-dimethyl-4-pivaloyloxyphenyl)- 5,7-di-tert-butyl-benzofuran-2-one.

The compounds of the present invention can also be used as stabilizers, especially as light stabilizers, for the major part of the materials known in the art of photographic reproduction and other reproduction techniques, for example as described in Research Disclosure 1990, 31429 (pages 474–480).

Several examples of the preparation and use of the compounds of the formula (I) are reported for a more detailed illustration of the present invention; these examples are given solely for illustrative purposes and do not imply any restriction. The compounds disclosed in Examples 2, 4, 8 and 9 are particularly preferred.

EXAMPLE 1

Preparation of 1-cyclohexyloxy-4-[3-diethoxymethylsilyl)propoxy]-2,2,6,6-tetramethylpiperidine 29.5 g (0.1 mol) of 4-allyloxy-1-cyclohexyloxy-2,2,6,6-tetramethylpiperidine, 16.1 g (0.12 mol) of diethoxymethylsilane and 0.01 g of $PtCl_2$ $(C_6H_5CH=CH_2)_2$ are heated for 1 hour at 90° C. and 1 hour at 125° C.

After cooling to ambient temperature, 50 ml of toluene are added and the resulting solution is filtered and evaporated at 50° C./1 mbar.

The residue is purified by distillation in vacuo, giving the product as a pale oil of boiling point=180°–181° C./0.1 mbar. Analysis for $C_{23}H_{47}NO_4Si$ Calculated: C=64.29%; H=11.02%; N=3.26% Found: C=64.25%; H=11.04%; N=3.25%

EXAMPLE 2

Preparation of a polysiloxane containing recurring units of the formula

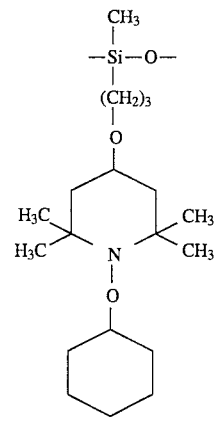

16.3 g (0.038 mol) of 1-cyclohexyloxy-4-[3-(diethoxymethylsilyl)propoxy]- 2,2,6,6-tetramethylpiperidine are dissolved at ambient temperature in 115 ml of 1N HCl and the resulting solution is stirred for 10 hours at 20° C. 80 ml of toluene are added and, while maintaining the temperature at 20° C., a solution of 5.2 g (0.13 mol) of NaOH in 30 ml of water is added. The mixture is stirred for 30 minutes and the organic phase is separated off, dried over anhydrous $Na_2SO_4$ and evaporated at 50° C./1 mbar.

The product is obtained as a yellow oil of $\overline{M}n=2650$.

EXAMPLE 3

Preparation of 1-methoxy-4-[3-diethoxymethylsilyl)propoxy]-2,2,6,6-tetramethylpiperidine 1 ml of a 2% solution of hexachloroplatinic acid in isopropanol is added to a mixture of 22.7 g (0.1 mol) of 4-allyloxy-1-methoxy-2,2,6,6-tetramethylpiperidine and 17.9 g (0.13 mol) of diethoxymethylsilane.

The reaction mixture is heated at 100° C. for 3 hours and then stirred in vacuo at ambient temperature for 3 hours.

After evaporation in vacuo at 50° C./1 mbar, the residue is purified by distillation in vacuo, giving the product as a pale oil of boiling point 104°–110° C./0.04 mbar, whose NMR and MS analyses conform with the indicated structure.

EXAMPLE 4

Preparation of a polysiloxane containing recurring units of the formula

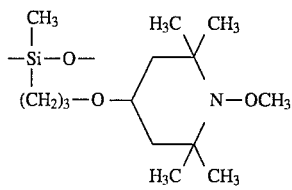

A mixture of 21.0 g (0.058 mol)of 1-methoxy-4-[3-(diethoxymethylsilyl)propoxy]- 2,2,6,6-tetramethylpiperidine, 1.02 g (0.003 mol) of butyl-tin diacetate and 3.0 g of water in 100 ml of xylene are heated at 120° C. for 2 hours.

The reaction mixture is cooled and extracted with toluene, and the organic phase is washed with water, dried over anhydrous sodium sulfate, filtered and evaporated at 50° C./1 mbar. The product is obtained as a viscous pale oil of $\overline{M}n=2300$.

EXAMPLE 5

Preparation of 1-methoxy-4-[3-[bis(trimethylsiloxy)methylsilyl] propoxy]- 2,2,6,6-tetramethylpiperidine Following the procedure of Example 3, 34.1 g (0.15 mol) of 4-allyloxy-1-methoxy-2,2,6,6-tetramethylpiperidine are reacted with 33.4 g (0.15 mol) of bis(trimethylsiloxy)methylsilane in the presence of 1 ml of a 2% solution of hexachloroplatinic acid in isopropanol.

The product is obtained as a clear oil of boiling point 125°–130° C./0.11 mbar. Analysis for $C_{20}H_{47}NO_4Si_3$ Calculated: C=53.40%; H=10.53%; N=3.11% Found: C=53.10%; H=11.00%; N=3.90%

EXAMPLE 6

Preparation of 2,4,6,8-tetramethyl-2,4,6,8-tetrakis[1-methoxy-4-(3-propoxy)-2,2,6,6-tetramethyl-4-piperidyl]-[1,3,5,7,2,4,6,8]-tetraoxatetrasilane Following the procedure of Example 3, 31.8 g (0.14 mol) of 4-allyloxy-1-methoxy-2,2,6,6-tetramethylpiperidine are reacted with 7.2 g (0.03 mol) of 2,4,6,8-tetramethyl-[1,3,5,7,2,4,6,8]-tetraoxatetrasilane in the presence of 1.0 ml of a 2% solution of hexachloroplatinic acid in isopropanol.

After the excess reagent has been distilled off, the product is obtained as a pale viscous oil. Analysis for $C_{56}H_{116}N_4O_{12}Si_4$ Calculated: C=58.49%; H=10.17%; N=4.87% Found: C=58.60%; H=10.80%; N=5.50%

EXAMPLE 7

Preparation of 1-methoxy-4-[bis(trimethylsiloxy)methylsilyl]-2,2,6,6-tetramethyl-4-oxypiperidine A solution of 22.2 g (0.12 mol) of 1-methoxy-2,2,6,6-tetramethyl-4-hydroxypiperidine, 26.4 g (0.12 mol) of bis(trimethylsiloxy)methylsilane and 0.02 g (0.12 mol) of cyclooctadiene-platinum diiodide in 45 ml of xylene is heated under reflux for 4 hours.

The solvent is evaporated at 50° C./1 mbar, and the residue is dissolved in n-heptane and purified on a silica gel column using n-heptane as solvent.

After evaporation of the solvent, the product is obtained as a pale oil. Analysis for $C_{17}H_{41}NO_4Si_3$ Calculated: C=50.07%; H=10.13%; N=3.43% Found: C=50.30%; H=10.90%; N=4.10%

EXAMPLE 8

Preparation of a polysiloxane of the formula

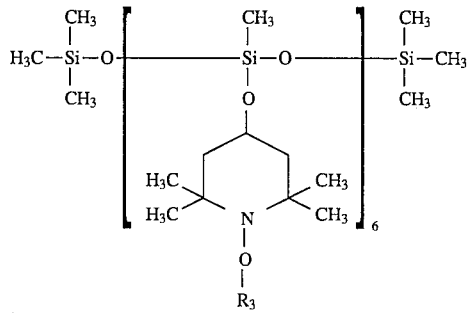

Following the procedure of Example 7, 25.7 g (0.14 mol) of 1-methoxy-2,2,6,6-tetramethyl-4-hydroxypiperidine are reacted with 9.7 g (0.025 mol) of the respective polymethylhydroxysiloxane in the presence of 11.5 mg of cyclooctadiene-platinum diiodide in 50 ml of xylene.

After evaporation of the solvent and purification by column chromatography, the product is obtained as a viscous pale oil whose NMR and MS analyses conform with the indicated structure.

EXAMPLE 9

Preparation of a polysiloxane of the formula

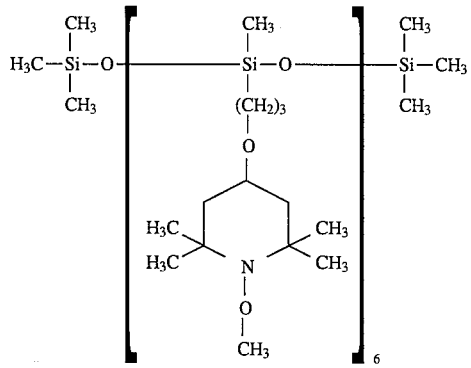

Following the procedure of Example 3, 27.3 g (0.12 mol) of 4-allyloxy-1-methoxy-2,2,6,6-tetramethylpiperidine are reacted with 7.8 g (0.02 mol) of the respective polymethylhydrosiloxane in the presence of 0.5 ml of a 2% solution of hexachloroplatinic acid in isopropanol. After heating at 120° C. for 4 hours, the solvent is dried off and after purification by column chromatography, the product is obtained as a viscous pale oil whose NMR and MS analyses conform with the indicated structure.

EXAMPLE 10

Light-stabilizing action in polypropylene fibres 2.5 g of the product indicated in Table 1, 1 g of tris(2,4-di-t-butylphenyl) phosphite, 0.5 g of calcium monoethyl 3,5-di-t-butyl-4-hydroxybenzylphosphonate, 1 g of calcium stearate and 2.5 g of titanium dioxide are mixed in a slow mixer with 1000 g of polypropylene powder of melt index= 12 g/10 minutes (measured at 230° C. and 2.16 kg).

The mixtures are extruded at 200°–230° C. to give polymer granules which are then converted into fibres, using a pilot-type apparatus (®Leonard-Sumirago (VA) Italy) operating under the following conditions:

Extruder temperature: 230°–245° C.
Head temperature: 255°–260° C.
Stretch ratio: 1:3.5
Count: 11 dtex per filament The fibres thus prepared are exposed, mounted on a white card, in a model 65 WR Weather—O—Meter (ASTM D2565-85) with a black panel temperature of 63° C. The residual tenacity is measured on samples taken after various times of exposure to light by means of a constant-speed dynamometer, and the exposure time in hours ($T_{50}$) needed to halve the initial tenacity is then calculated. Fibres prepared under the same conditions as indicated above, but without addition of stabilizers according to the invention, arc exposed for comparison.

The results obtained are shown in Table 1:

TABLE 1

| Stabilizer | $T_{50}$ (hours) |
| --- | --- |
| None | 220 |
| Compound from Example 1 | 1910 |

What is claimed is:

1. A compound of the formula (I)

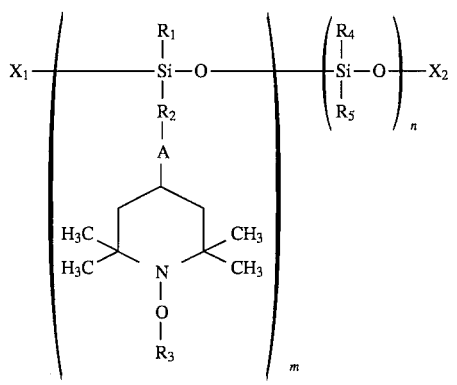

in which m+n is a number from 1 to 100 and n varies from zero to 90% of the sum of m+n, A is —O— or

where $R_6$ is hydrogen, $C_1$–$C_{18}$alkyl or a group of the formula (II)

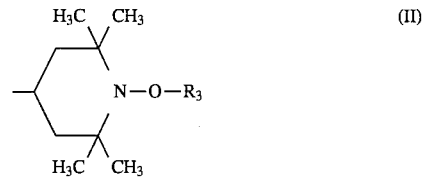

$R_1$ and $R_4$ which can be identical or different are $C_1$–$C_8$alkyl, phenyl, $C_1$–$C_8$alkoxy, OH, ONa or OK, $R_2$ is $C_2$–$C_{12}$alkylene or also a direct bond if A is —O— and $R_1$ and $R_4$ are $C_1$–$C_8$alkyl or phenyl, $R_3$ is $C_1$–$C_{18}$alkyl, $C_5$–$C_{12}$cycloalkyl, $C_2$–$C_{18}$alkenyl, $C_5$–$C_{12}$cycloalkenyl, $C_7$–$C_{12}$aralkyl, a saturated or unsaturated radical of a bicyclic or tricyclic $C_7$–$C_{12}$hydrocarbon or $C_6$–$C_{10}$aryl which is unsubstituted or substituted by $C_1$–$C_8$alkyl, $R_5$ is hydrogen, $C_1$–$C_{18}$alkyl, $C_5$–$C_{12}$cycloalkyl or phenyl, $X_1$ is as defined for $R_1$ or is a group $(R_7)_3$SiO— with $R_7$ being $C_1$–$C_8$alkyl, $X_2$ is hydrogen, Na, K, $C_1$–$C_8$alkyl, a group $(R_7)_3$Si— or, if n is zero and $R_1$ and $X_1$ are $C_1$–$C_8$alkyl or phenyl, $X_2$ is also a group of the formula (III)

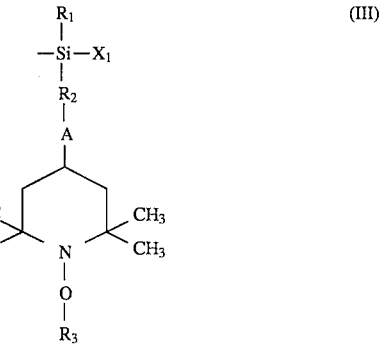

and, if m+n is a number from 3 to 10, $X_1$ and $X_2$ together can also be a direct bond.

2. A compound of the formula (I) according to claim 1, in which m+n is a number from 1 to 80, n varies from zero to 90% of the sum m+n, A is —O— or

where $R_6$ is hydrogen, $C_1$–$C_{12}$alkyl or a group of the formula (II), $R_1$ and $R_4$ which can be identical or different are $C_1$–$C_6$alkyl, phenyl, $C_1$–$C_6$ alkoxy, OH, ONa or OK, $R_2$ is $C_2$–$C_8$alkylene or also a direct bond if A is —O— and $R_1$ and $R_4$ are $C_1$–$C_6$alkyl or phenyl, $R_3$ is $C_1$–$C_{18}$alkyl, $C_5$–$C_8$cycloalkyl, $C_3$–$C_{12}$alkenyl, $C_5$–$C_8$cycloalkenyl, $C_7$–$C_9$aralkyl, a saturated or unsaturated radical of a bicyclic or tricyclic $C_7$–$C_m$ hydrocarbon or $C_6$–$C_{10}$aryl which is unsubstituted or substituted by $C_1$–$C_4$alkyl, $R_5$ is hydrogen, $C_1$-$C_{18}$alkyl, $C_5$-$C_8$cycloalkyl or phenyl, $X_1$ is as defined for $R_1$ or is a group $(R_7)_3SiO-$ with $R_7$ being $C_1$-$C_6$alkyl, $X_2$ is hydrogen, Na, K, $C_1$-$C_6$alkyl, a group $(R_7)_3Si-$ or, if n is zero and $R_1$ and $X_1$ are $C_1$-$C_6$alkyl or phenyl, $X_2$ is also a group of the formula (III) and, if m+n is a number from 3 to 10, $X_1$ and $X_2$ together can also be a direct bond.

3. A compound of the formula (I) according to claim 1, in which m+n is a number from 1 to 60, n varies from zero to 90% of the sum of m+n, A is —O— or

where $R_6$ is hydrogen or $C_1$-$C_8$alkyl, $R_1$ and $R_4$ which can be identical or different are $C_1$-$C_4$alkyl, phenyl, $C_1$-$C_4$alkoxy, OH, ONa or OK, $R_2$ is $C_2$-$C_6$alkylene or also a direct bond if A is —O— and $R_1$ and $R_4$ are $C_1$-$C_4$alkyl or phenyl, $R_3$ is $C_1$-$C_{16}$alkyl, $C_5$-$C_7$cycloalkyl, $C_3$-$C_6$alkenyl, $C_5$-$C_7$ cycloalkenyl, benzyl, α-methylbenzyl, α,α-dimethylbenzyl, bicycloheptyl, bicycloheptenyl, decahydronaphthyl or tetrahydronaphthyl, $R_5$ is hydrogen, $C_1$-$C_{16}$alkyl, cyclohexyl or phenyl, $X_1$ is as defined for $R_1$ or a group $(R_7)_3SiO-$ with $R_7$ being $C_1$-$C_4$alkyl, $X_2$ is hydrogen, Na, K, $C_1$-$C_4$alkyl, a group $(R_7)_3Si-$ or, if n is zero and $R_1$ and $X_1$ are $C_1$-$C_4$alkyl or phenyl, $X_2$ is also a group of the formula (III) and, if m+n is a number from 3 to 10, $X_1$ and $X_2$ together can also be a direct bond.

4. A compound of the formula (I) according to claim 1, in which m+n is a number from 1 to 50, n varies from zero to 75% of the sum m+n, A is —O— or

where $R_6$ is hydrogen or $C_1$-$C_4$alkyl, $R_1$ and $R_4$ which can be identical or different are $C_1$-$C_3$alkyl, $C_1$-$C_3$alkoxy or OH, $R_2$ is $C_2$-$C_4$alkylene or is also a direct bond if A is —O— and $R_1$ and $R_4$ are $C_1$-$C_3$alkyl, $R_3$ is methyl, $C_6$-$C_{12}$alkyl, cyclopentyl, cyclohexyl, methylcyclohexyl or α-methylbenzyl, $R_5$ is hydrogen, $C_1$-$C_{14}$alkyl or cyclohexyl, $X_1$ is as defined for $R_1$ or is a group $(R_7)_3SiO-$ with $R_7$ being $C_1$-$C_3$alkyl, $X_2$ is hydrogen, $C_1$-$C_3$alkyl, a group $(R_7)_3Si-$ or, if n is zero and $R_1$ and $X_1$ are $C_1$-$C_3$alkyl, $X_2$ is also a group of the formula (III) and, if m+n is a number from 3 to 10, $X_1$ and $X_2$ together can also be a direct bond.

5. A compound of the formula (I) according to claim 1, in which m+n is a number from 1 to 40, n varies from zero to 50% of the sum m+n, A is —O—, $R_1$ and $R_4$ which can be identical or different are methyl, methoxy, ethoxy or OH, $R_2$ is trimethylene or is also a direct bond if A is —O— and $R_1$ and $R_4$ are methyl, $R_3$ is methyl, $C_7$-$C_9$alkyl or cyclohexyl, $R_5$ is $C_1$-$C_{12}$alkyl, $X_1$ is as defined for $R_1$ or is a group $(CH_3)_3SiO-$ and $X_2$ is hydrogen, methyl, ethyl, a group $(CH_3)_3Si-$ or, if n is zero and $R_1$ and $X_1$ are methyl, $X_2$ is also a group of the formula (III) and, if m+n is a number from 3 to 10, $X_1$ and $X_2$ together can also be a direct bond.

6. A compound of the formula (I) according to claim 1, which corresponds to

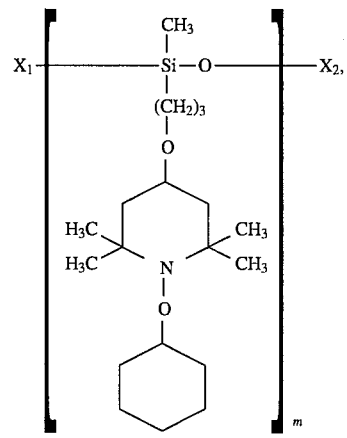

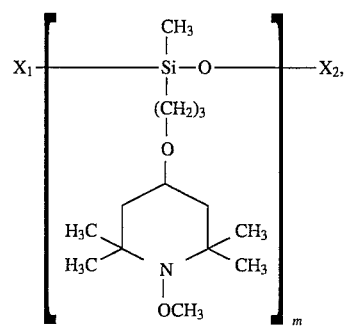

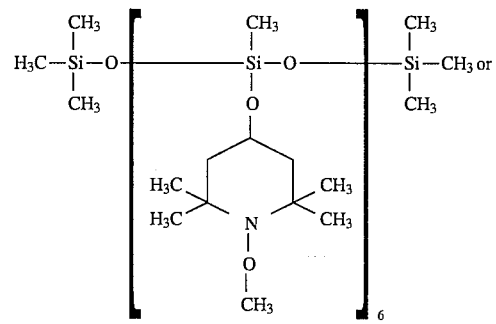

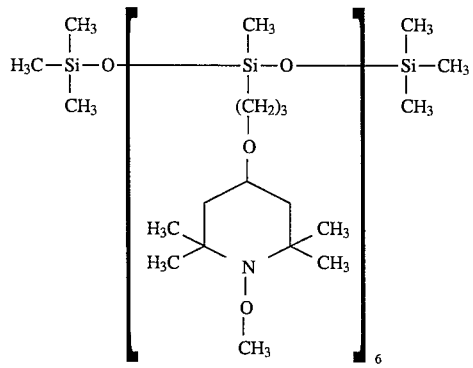

wherein $X_1$, $X_2$ and m are as defined in claim 1.

7. A composition which contains a material susceptible to degradation induced by light, heat and oxidation and at least one compound of the formula (I) according to claim 1.

8. A composition according to claim 7, wherein the organic material is a synthetic polymer.

9. A composition according to claim 8, which contains other conventional additives for synthetic polymers, in addition to the compounds of the formula (I).

10. A composition according to claim 7, wherein the organic material is a polyolefin.

11. A composition according to claim 7, wherein the organic material is polyethylene or polypropylene.

12. A method for stabilizing an organic material against degradation induced by light, heat and oxidation, which comprises incorporating into said material at least one compound of the formula (I) according to claim 1.

* * * * *